United States Patent [19]

Tsukazaki et al.

[11] Patent Number: 5,777,213

[45] Date of Patent: Jul. 7, 1998

[54] PREPARATIVE LIQUID CHROMATOGRAPHY APPARATUS

[75] Inventors: Hideo Tsukazaki, Toride; Kazuya Akaike, Tokyo, both of Japan

[73] Assignee: TFC Corporation, Tokyo, Japan

[21] Appl. No.: 752,589

[22] Filed: Nov. 21, 1996

[51] Int. Cl.[6] .......................... G01N 31/08; B01D 15/08
[52] U.S. Cl. .................. 73/61.52; 73/61.56; 422/68.1; 422/70; 137/7; 137/897; 137/606
[58] Field of Search .................. 73/61.52, 61.55, 73/61.56, 61.57; 422/70, 68.1; 137/7, 606, 897

[56] References Cited

U.S. PATENT DOCUMENTS

| | | | |
|---|---|---|---|
| 3,298,383 | 1/1967 | Cooper | 137/3 |
| 3,721,253 | 3/1973 | Remke | 137/3 |
| 4,111,637 | 9/1978 | Hillman, II | 431/12 |
| 4,116,046 | 9/1978 | Stein | 73/61.1 C |
| 4,165,219 | 8/1979 | Huber | 23/230 R |
| 4,239,623 | 12/1980 | Schrenker | 210/96.1 |
| 4,275,752 | 6/1981 | Collier et al. | 137/7 |
| 4,286,457 | 9/1981 | Johnson, Jr. | 73/53 |
| 4,478,246 | 10/1984 | Sherrod | 137/557 |
| 4,596,156 | 6/1986 | Shimizu et al. | 73/863.31 |
| 4,631,687 | 12/1986 | Kowalski et al. | 364/497 |
| 4,669,502 | 6/1987 | Lonardi et al. | 137/624.18 |
| 4,849,110 | 7/1989 | Takata et al. | 210/656 |
| 4,882,781 | 11/1989 | Allington | 364/510 |
| 4,886,090 | 12/1989 | Hays | 137/624.11 |
| 4,913,180 | 4/1990 | Anderson, Jr. | 137/1 |
| 4,920,056 | 4/1990 | Dasgupta | 436/50 |
| 4,988,447 | 1/1991 | Hellinger | 210/659 |
| 4,989,632 | 2/1991 | Bauerle | 137/343 |
| 4,989,637 | 2/1991 | Dittrich | 137/599 |
| 5,093,267 | 3/1992 | Miura et al. | 436/93 |
| 5,135,718 | 8/1992 | Kawaguchi et al. | 422/70 |
| 5,179,970 | 1/1993 | Jarocki et al. | 137/9 |
| 5,181,538 | 1/1993 | Manganaro | 137/607 |
| 5,325,889 | 7/1994 | Paul et al. | 137/594 |
| 5,358,177 | 10/1994 | Cashmore | 236/12.12 |
| 5,609,180 | 3/1997 | Moore et al. | 137/101.19 |

FOREIGN PATENT DOCUMENTS 64-44847  2/1989  Japan ............... G01N 30/02

Primary Examiner—Hezron E. Williams
Assistant Examiner—J. David Wiggins
Attorney, Agent, or Firm—Sughrue, Mion, Zinn, Macpeak & Seas, PLLC

[57] ABSTRACT

The invention provides a preparative liquid chromatography apparatus wherein flow rate control can be effected in a wider range and with a higher degree of accuracy than where a pump is used while preventing production of air bubbles in liquid and the mixture ratio of chemicals can be controlled in a wide range and with a high degree of accuracy. The preparative liquid chromatography apparatus includes a plurality of buffer liquid tanks of the enclosed pressurizing type, a pressurization apparatus for supplying gas to apply a pneumatic pressure to the insides of the buffer liquid tanks, a plurality of electric signal to pneumatic pressure converters for adjusting pneumatic pressures of the gas to be applied actually to the buffer liquid tanks by the pressurization apparatus in response to electric signals, a plurality of flow rate detectors for detecting flow rates of liquid forced out from the buffer liquid tanks by the pneumatic pressures of the gas, and arithmetic units for comparing the flow rates detected by the flow rate detectors with preset values to produce electric signals to be outputted to the electric signal to pneumatic pressure converters.

6 Claims, 4 Drawing Sheets

PREPARATIVE LIQUID CHROMATOGRAPHY APPARATUS

BACKGROUND OF THE INVENTION

1. Field of the Invention

This invention relates to a preparative liquid chromatography apparatus used for refining in a field of manufacture of medicine, food and so forth for which cleanliness is required.

2. Description of the Related Art

A preparative liquid chromatography apparatus of the type mentioned conventionally has such a general construction as shown in FIG. 4. Referring to FIG. 4, the liquid crystal chromatography apparatus shown includes a plurality of buffer liquid tanks 21 and 22 of the type open to the atmospheric air, a plurality of liquid feed pumps 23 and 24 of the plunger type, piston type, diaphragm type, rotary type or some other suitable type connected to the secondary sides (exit sides) of the buffer liquid tanks 21 and 22, respectively, and a setting unit 25 for adjusting the rotating speeds or the reciprocating speeds of the liquid feed pumps 23 and 24 merely to values conforming to flow rates individually set for different liquids without effecting feedback control to control the mixture ratio of the chemicals.

Since the preparative liquid chromatography apparatus described above is constructed in such a manner as described above, it is disadvantageous in the following points.

(1) Since a pump is employed, liquid is decompressed on the primary side of the pump, and thereupon, dissolved gas in the liquid is decompressed to form air bubbles in the liquid. The air bubbles remain in the liquid until the liquid comes to the last end of a liquid feed line, and produce noise to a measuring instrument located there and besides have an influence upon the refining performance of a preparative column.

(2) Generally, the range of adjustment of a pump is approximately 1:10, and the adjustment particularly in a low flow rate region is so difficult that, even if feedback control is employed, control in a low flow rate region is not easy.

SUMMARY OF THE INVENTION

It is an object of the present invention to provide a preparative liquid chromatography apparatus wherein flow rate control can be effected in a wider range and with a higher degree of accuracy than where a pump is used while preventing production of air bubbles in liquid and the mixture ratio of chemicals can be controlled in a wide range and with a high degree of accuracy.

In order to attain the object described above, according to an aspect of the present invention, there is provided a preparative liquid chromatography apparatus, which comprises a plurality of buffer liquid tanks of the enclosed pressurizing type, a pressurization apparatus for supplying gas to apply a pneumatic pressure to the insides of the buffer liquid tanks, a plurality of electric signal to pneumatic pressure converters for individually adjusting pneumatic pressures of the gas to be applied actually to the buffer liquid tanks by the pressurization apparatus in response to respective electric signals, a plurality of flow rate detectors for individually detecting flow rates of liquid forced out from the buffer liquid tanks by the pneumatic pressures of the overhead gas, and arithmetic unit means for comparing the flow rates detected by the flow rate detectors with respective preset values to produce electric signals to be outputted individually to the electric signal to pneumatic pressure converters.

In the preparative liquid chromatography apparatus, the buffer liquid tanks are in an enclosed state, and a pneumatic pressure is applied to the insides of the buffer liquid tanks by the pressurization apparatus to force out liquid from the buffer liquid tanks. Then, the flow rates of the liquid thus forced out from the buffer liquid tanks are detected by the flow rate detectors, and the thus detected flow rates are compared with the respective preset values by the arithmetic unit means. Thereupon, the arithmetic unit means produces electric signals to feedback control the electric signal to pneumatic pressure converters to automatically adjust the pneumatic pressures of the gas to be applied actually to the buffer liquid tanks so that the flow rates of the liquid to be forced out from the buffer liquid tanks may individually be equal to the preset values.

According to another aspect of the present invention, there is provided a preparative liquid chromatography apparatus, which comprises a plurality of buffer liquid tanks of the enclosed pressurizing type, a pressurization apparatus for supplying gas to apply a pneumatic pressure to the insides of the buffer liquid tanks, a plurality of electric signal to pneumatic flow rate converters for individually adjusting flow rates of the gas to be supplied actually into the buffer liquid tanks by the pressurization apparatus in response to respective electric signals, a plurality of flow rate detectors for individually detecting flow rates of liquid forced out from the buffer liquid tanks by the pneumatic pressures of the gas, and arithmetic unit means for comparing the flow rates detected by the flow rate detectors with respective preset values to produce electric signals to be outputted individually to the electric signal to pneumatic flow rate converters.

In the preparative liquid chromatography apparatus, the buffer liquid tanks are in an enclosed state, and a pneumatic pressure is applied to the insides of the buffer liquid tanks by the pressurization apparatus to force out liquid from the buffer liquid tanks. Then, the flow rates of the liquid thus forced out from the buffer liquid tanks are detected by the flow rate detectors, and the thus detected flow rates are compared with the respective preset values by the arithmetic unit means. Thereupon, the arithmetic unit means produces electric signals to feedback control the electric signal to pneumatic flow rate converters to automatically adjust the flow rates of the gas to be supplied actually into the buffer liquid tanks so that the flow rates of the liquid to be forced out from the buffer liquid tanks may individually be equal to the preset values.

According to a further aspect of the present invention, there is provided a preparative liquid chromatography apparatus, which comprises a plurality of buffer liquid tanks of the enclosed pressurizing type, a pressurization apparatus for supplying gas to apply a fixed pneumatic pressure to the insides of the buffer liquid tanks, a plurality of flow rate control valves for individually controlling flow rates of liquid forced out from the buffer liquid tanks in response to respective electric signals, a plurality of flow rate detectors for individually detecting the flow rates of the liquid forced out from the buffer liquid tanks by the pneumatic pressures of the gas, and arithmetic unit means for comparing the flow rates detected by the flow rate detectors with respective preset values to produce electric signals to be outputted individually to the flow rate control valves.

In the preparative liquid chromatography apparatus, the buffer liquid tanks are in an enclosed state, and a fixed pneumatic pressure is applied to the insides of the buffer liquid tanks by the pressurization apparatus to force out liquid from the buffer liquid tanks. Then, the flow rates of the liquid thus forced out from the buffer liquid tanks are detected by the flow rate detectors, and the thus detected flow rates are compared with the respective preset values by the arithmetic unit means. Thereupon, the arithmetic unit means produces electric signals to feedback control the flow rate control valves so that the flow rates of the liquid forced out from the buffer liquid tanks may individually be equal to the preset values.

Preferably, any of the preparative liquid chromatography apparatus further comprises a restrictor provided for a liquid feed line system, provided for feeding the liquid from the buffer liquid tanks, for keeping the liquid in the liquid feed line system in a pressurized state similarly as in the insides of the buffer liquid tanks, or/and the pressurization apparatus employs nitrogen gas to apply the pneumatic pressure to the insides of the buffer liquid tanks.

The preparative liquid chromatography apparatus of the present invention described above present various advantages. In particular, since the buffer liquid tanks are in an enclosed state and liquid is forced out from within the buffer liquid tanks by supplying gas into them to apply a pneumatic pressure to the insides of them by means of the pressurization apparatus, such an apparatus as a pump which has a complicated internal structure is not required for a liquid feed line, particularly for a liquid feed line for medicine or food which requires cleanliness. Consequently, the preparative liquid chromatography apparatus are simplified in structure and improved in cleanliness comparing with conventional preparative liquid chromatography apparatus. Further, production of air bubbles is eliminated. Besides, flow rate control can be effected over a wider range and with a higher degree of accuracy than where a pump is used, and the mixture ratio of chemicals can be controlled over a wide range and with a high degree of accuracy.

Where a restrictor is provided for a liquid feed line system, the liquid in the liquid feed line system from the buffer liquid tanks is kept in a pressurized state similarly as in the insides of the buffer liquid tanks, and consequently, production of air bubbles can be prevented over the overall length of the liquid feed line system from a supply source of the liquid to the last end of the liquid feed line system. Further, where the pressurization apparatus employs nitrogen gas to apply the pneumatic pressure to the insides of the buffer liquid tanks, the preparative liquid chromatography apparatus are superior in safety.

The above and other objects, features and advantages of the present invention will become apparent from the following description and the appended claims, taken in conjunction with the accompanying drawings in which like parts or elements are denoted by like reference characters.

DESCRIPTION OF THE PREFERRED EMBODIMENTS

Figure 1:
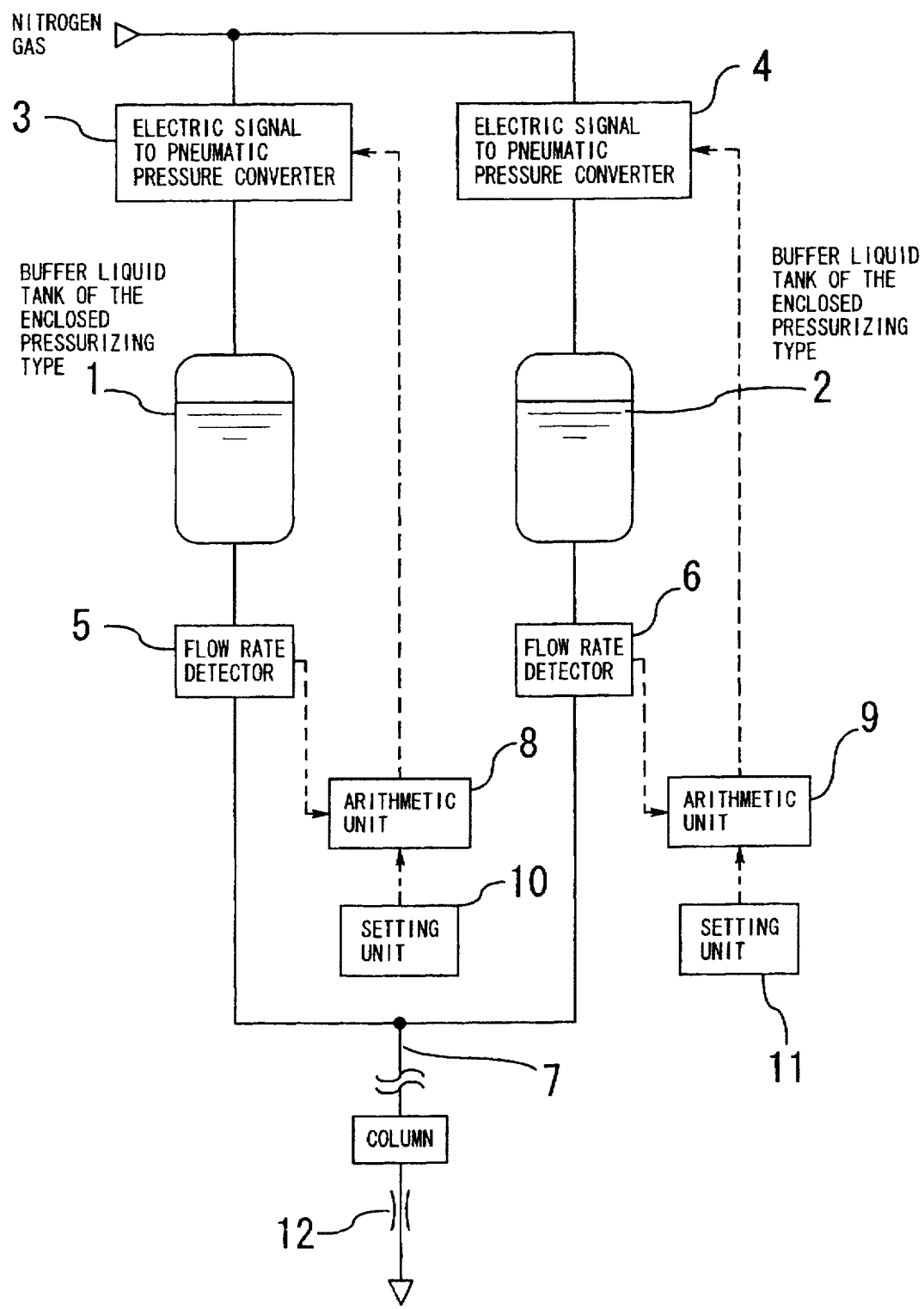
FIG. 1 is a block diagram of a preparative liquid chromatography apparatus showing a preferred embodiment of the present invention.

Referring to FIG. 1, there is shown a preparative liquid chromatography apparatus according to a first preferred embodiment of the present invention. The preparative liquid chromatography apparatus shown includes a pair of buffer liquid tanks 1 and 2 of the enclosed pressurizing type, a pair of electric signal to pneumatic pressure converters 3 and 4 connected to the primary sides (upper sides) of the buffer liquid tanks 1 and 2, respectively, and a pair of flow rate detectors 5 and 6 connected to the secondary sides (lower sides) of the buffer liquid tanks 1 and 2, respectively. The primary sides of the electric signal to pneumatic pressure converters 3 and 4 are connected in parallel to each other to a common nitrogen gas supply source (not shown) by a pipe system. Meanwhile, the secondary sides of the flow rate detectors 5 and 6 are connected to a common liquid feed line system 7 so that they may join liquids from the buffer liquid tanks 1 and 2 to form a single flow.

An arithmetic unit 8 for performing feedback control by PID (proportional integral differential) operation is electrically connected between the electric signal to pneumatic pressure converter 3 and the flow rate detector 5, and another arithmetic unit 9 similar to the arithmetic unit 8 is electrically connected between the electric signal to pneumatic pressure converter 4 and the flow rate detector 6. Further, a pair of setting units 10 and 11 for varying the mixture ratio of liquids from the buffer liquid tanks 1 and 2 with respect to time are connected to the arithmetic units 8 and 9, respectively. Each of the arithmetic units 8 and 9 compares a flow rate detected by the flow rate detector 5 or 6 with a set value of the arithmetic unit 8 or 9 and outputs, in response to a difference between them, an electric signal for controlling the electric signal to pneumatic pressure converter 3 or 4. Further, a restrictor 12 is provided at the last stage of the liquid feed line system 7 so that liquid is kept in a pressurized state (positively pressurized state) without being decompressed in the liquid feed line system 7 within the flow path range from the buffer liquid tanks 1 and 2 to the restrictor 12.

Since nitrogen gas is forced into each of the buffer liquid tanks 1 and 2 with a pressure adjusted by the electric signal to pneumatic pressure converter 3 or 4, liquid in the buffer liquid tank 1 or 2 is forced out with a flow rate conforming to the pressure. The flow rate of the liquid thus forced out is detected by the flow rate detector 5 or 6, and if a difference is detected between the thus detected flow rate and the set value of the setting unit 10 or 11, then the electric signal to pneumatic pressure converter 3 or 4 is feedback controlled by the arithmetic unit 5 or 6 so that the difference may be modified or removed. In this instance, since the range of adjustment of the electric signal to pneumatic pressure converter 3 or 4 sufficiently satisfies the control range of 1:20 of the liquid flow rate, liquid mixture ratio control can be effected over a wide rage. Besides, since the feedback control is effected constantly, the control is effected with a very high degree of accuracy. Further, since the liquid normally remains in a pressurized state while it is fed from the buffer liquid tank 1 or 2 to the restrictor 12 as described above, no bubbles are produced in the buffer liquid tank 1 or 2 and in the liquid feed line from the buffer liquid tank 1 or 2 to the last stage.

A prototype of the preparative liquid chromatography apparatus according to the present invention was produced, and using the prototype, the control accuracy and production of air bubbles were confirmed setting the joined flow rate of two liquids to a fixed value and varying the rates of them from 0 to 100% and from 100 to 0%. As a result of the control, a linearity of 0.5% was confirmed within the range of the ratio of 5 to 98%. Further, the liquids were flowed in a transparent tube and production of air bubbles on the secondary side was observed. The observation revealed no production of air bubbles.

Figure 2:
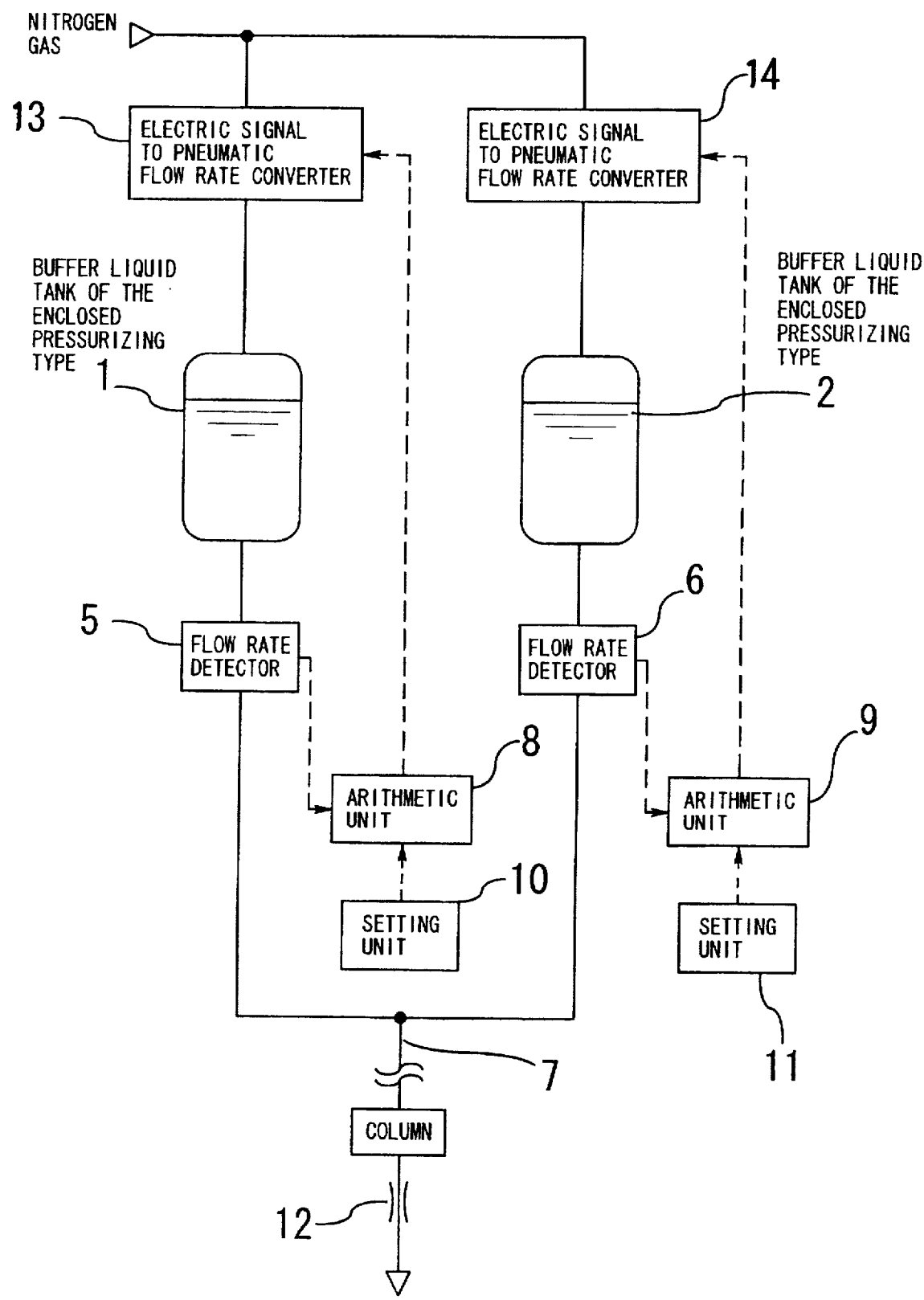
FIG. 2 is a block diagram of another preparative liquid chromatography apparatus showing another preferred embodiment of the present invention.

FIG. 2 shows a preparative liquid chromatography apparatus according to another preferred embodiment of the present invention. Referring to FIG. 2, the present preparative liquid chromatography apparatus is a modification to and is different from the preparative liquid chromatography apparatus of the first embodiment described hereinabove with reference to FIG. 1 only in that electric signal to pneumatic flow rate converters 13 and 14 are provided in place of the electric signal to pneumatic pressure converters 3 and 4 so that the flow rates of nitrogen gas to be supplied into the buffer liquid tanks 1 and 2 are feedback controlled to adjust the flow rates of liquid from the buffer liquid tanks 1 and 2, respectively.

Figure 3:
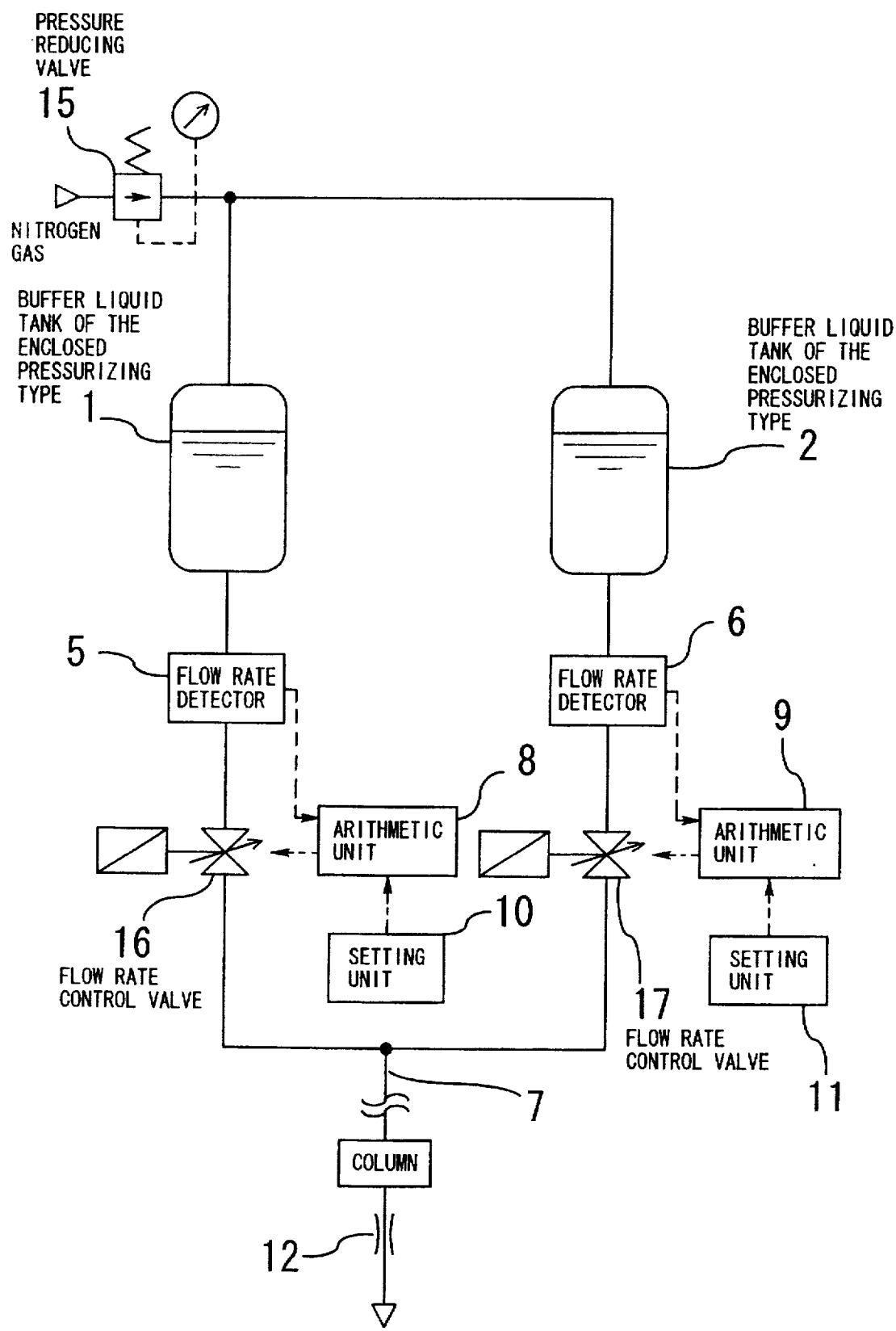
FIG. 3 is a block diagram of a further preparative liquid chromatography apparatus showing a further preferred embodiment of the present invention.
Figure 4:
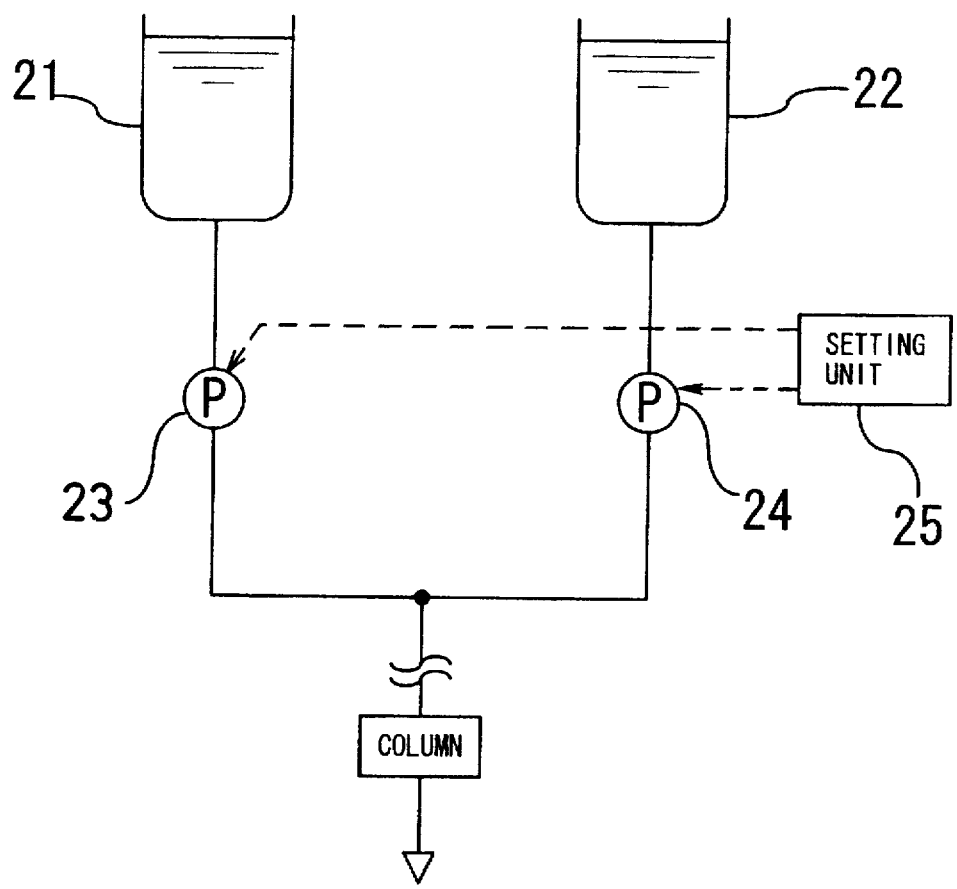
FIG. 4 is a block diagram showing a conventional preparative liquid chromatography apparatus.

FIG. 3 shows a preparative liquid chromatography apparatus according to a further preferred embodiment of the present invention. Referring to FIG. 3, the present preparative liquid chromatography apparatus is a modification to and is different from the preparative liquid chromatography apparatus of the first embodiment described hereinabove with reference to FIG. 1 in that it includes, in place of the electric signal to pneumatic pressure converters 3 and 4, a pressure reducing valve 15 for controlling the pressure of nitrogen gas to be forced into the buffer liquid tanks 1 and 2 and additionally includes a pair of flow rate control valves 16 and 17 provided at the following stages to the flow rate detectors 5 and 6, respectively. Detection flow rates detected by the flow rate detectors 5 and 6 are compared with set values of the setting units 10 and 11 by the arithmetic units 8 and 9, and the flow rate control valves 16 and 17 are controlled with results of the comparison, respectively, so that the flow rates of liquids to be forced out from the buffer liquid tanks 1 and 2 may be equal to the set values.

It is to be noted that, while the preparative liquid chromatography apparatus of the first to third embodiments described above include a pair of buffer liquid tanks of the enclosed pressurizing type in order to mix two different kinds of liquids, the present invention can be applied also to preparative liquid chromatography apparatus wherein three or more different kinds of liquids are mixed using three or more buffer liquid tanks of the enclosed pressurizing type.

Having now fully described the invention, it will be apparent to one of ordinary skill in the art that many changes and modifications can be made thereto without departing from the spirit and scope of the invention as set forth herein.

The invention claimed is:

1. A preparative liquid chromatography apparatus for detecting, comparing and controlling the flow rates of a plurality of buffer liquids to be delivered towards a chromatography column, comprising:

a plurality of buffer liquid tanks of the enclosed pressurizing type;

a pressurization apparatus for supplying gas to apply a pneumatic pressure to the insides of said buffer liquid tanks;

a plurality of electric signal to pneumatic pressure converters for individually adjusting pneumatic pressures of the gas to be applied actually to said buffer liquid tanks by said pressurization apparatus in response to respective electric signals;

a plurality of flow rate detectors for individually detecting flow rates of liquid forced out from said buffer liquid tanks by the pneumatic pressures of the gas; and arithmetic unit means for comparing the flow rates detected by said flow rate detectors with respective preset values to produce electric signals to be outputted individually to said electric signal to pneumatic pressure converters.

2. A preparative liquid chromatography apparatus for detecting, comparing and controlling the flow rates of a plurality of buffer liquids to be delivered towards a chromatography column, comprising:

a plurality of buffer liquid tanks of the enclosed pressurizing type;

a pressurization apparatus for supplying gas to apply a pneumatic pressure to the insides of said buffer liquid tanks;

a plurality of electric signal to pneumatic flow rate converters for individually adjusting flow rates of the gas to be supplied actually into said buffer liquid tanks by said pressurization apparatus in response to respective electric signals;

a plurality of flow rate detectors for individually detecting flow rates of liquid forced out from said buffer liquid tanks by the pneumatic pressures of the gas; and arithmetic unit means for comparing the flow rates detected by said flow rate detectors with respective preset values to produce electric signals to be outputted individually to said electric signal to pneumatic flow rate converters.

3. A preparative liquid chromatography apparatus for detecting, comparing and controlling the flow rates of a plurality of buffer liquids to be delivered towards a chromatography column, comprising:

a plurality of buffer liquid tanks of the enclosed pressurizing type;

a pressurization apparatus for supplying gas to apply a fixed pneumatic pressure to the insides of said buffer liquid tanks;

a plurality of flow rate control valves for individually controlling flow rates of liquid forced out from said buffer liquid tanks in response to respective electric signals;

a plurality of flow rate detectors for individually detecting the flow rates of the liquid forced out from said buffer liquid tanks by the pneumatic pressures of the gas; and arithmetic unit means for comparing the flow rates detected by said flow rate detectors with respective preset values to produce electric signals to be outputted individually to said flow rate control valves.

4. A preparative liquid chromatography apparatus as claimed in any one of claims 1 to 3, further comprising a restrictor provided for a liquid feed line system, provided for feeding the liquid from said buffer liquid tanks, for keeping the liquid in said liquid feed line system in a pressurized state similarly as in the insides of said buffer liquid tanks.

5. A preparative liquid chromatography apparatus as claimed in any one of claims 1 to 3, wherein said pressurization apparatus employs nitrogen gas to apply the pneumatic pressure to the insides of said buffer liquid tanks.

6. A preparative liquid chromatography apparatus as claimed in any one of claims 1 to 3, further comprising a restrictor provided for a liquid feed line system, provided for feeding the liquid from said buffer liquid tanks, for keeping the liquid in said liquid feed line system in a pressurized state similarly as in the insides of said buffer liquid tanks, and wherein said pressurization apparatus employs nitrogen gas to apply the pneumatic pressure to the insides of said buffer liquid tanks.

\* \* \* \* \*